(12) United States Patent
Wacker

(10) Patent No.: US 9,956,962 B2
(45) Date of Patent: May 1, 2018

(54) METHOD AND DEVICE FOR DETERMINING A REACTION TIME OF A VEHICLE DRIVER

(71) Applicant: Robert Bosch GmbH, Stuttgart (DE)

(72) Inventor: Esther-Sabrina Wacker, Hildesheim (DE)

(73) Assignee: ROBERT BOSCH GMBH, Stuttgart (DE)

( * ) Notice: Subject to any disclaimer, the term of this patent is extended or adjusted under 35 U.S.C. 154(b) by 13 days.

(21) Appl. No.: 14/823,131

(22) Filed: Aug. 11, 2015

(65) Prior Publication Data

US 2016/0046295 A1 Feb. 18, 2016

(30) Foreign Application Priority Data

Aug. 14, 2014 (DE) .......................... 10 2014 216 208

(51) Int. Cl.
*B60R 22/00* (2006.01)
*E05F 15/00* (2015.01)
(Continued)

(52) U.S. Cl.
CPC ............ *B60W 40/08* (2013.01); *A61B 3/0025* (2013.01); *A61B 3/113* (2013.01); *A61B 5/162* (2013.01);
(Continued)

(58) Field of Classification Search
CPC ....... A61B 3/113; A61B 3/0091; A61B 3/024; A61B 5/162; A61B 3/0025; A61B 5/16; A61B 5/18; A61B 3/022; A61B 3/028; A61B 3/032; A61B 3/066; A61B 3/18; A61B 5/1121; A61B 5/6898; A61B 2503/10; A61B 2562/0204; A61B 2562/0219; A61B 3/0033; A61B 3/005; A61B 3/02; A61B 3/036; A61B 3/063;
(Continued)

(56) References Cited

U.S. PATENT DOCUMENTS 5,801,667 A * 9/1998 Shimizu ................. H04N 7/183
340/435
5,813,993 A * 9/1998 Kaplan ................ A61B 5/0476
600/26
(Continued)

FOREIGN PATENT DOCUMENTS

WO 93/16637 A1 9/1993
WO 01/52722 A1 7/2001

*Primary Examiner* — Anne M Antonucci
*Assistant Examiner* — Kenny A. Taveras
(74) *Attorney, Agent, or Firm* — Norton Rose Fulbright US LLP; Gerard Messina

(57) ABSTRACT

A method and a device for determining a reaction time of a vehicle driver of a vehicle includes a display device displaying at least one visual stimulus; and processing circuitry using a view recognition device to observe the direction of view of the vehicle driver, and determining the reaction time starting from the displaying of the visual stimulus, the reaction time corresponding to a specified time span if the direction of view of the vehicle driver is not recognized within the specified time span as running in the direction of the visual stimulus, or the reaction time corresponding to a time span in which the direction of view of the vehicle driver is recognized within the specified time span as running in the direction of the visual stimulus.

14 Claims, 2 Drawing Sheets

(51) Int. Cl.
    *G05D 1/00*     (2006.01)
    *G05D 3/00*     (2006.01)
    *G06F 7/00*     (2006.01)
    *B60W 40/08*     (2012.01)
    *A61B 3/00*     (2006.01)
    *A61B 3/113*     (2006.01)
    *A61B 5/18*     (2006.01)
    *A61B 5/16*     (2006.01)

(52) U.S. Cl.
    CPC ....... *A61B 5/18* (2013.01); *B60W 2040/0827* (2013.01); *B60W 2040/0836* (2013.01); *B60W 2710/30* (2013.01)

(58) Field of Classification Search
    CPC ......... A61B 3/1015; A61B 3/11; A61B 3/112; A61B 3/145; A61B 5/0476; A61B 5/0488; A61B 5/0496; A61B 5/1112; A61B 5/1114; A61B 5/4076; A61B 5/6803; A61B 5/6814; A61B 5/6824; A61B 5/6828; A61B 5/726; A61B 5/7275; A61B 5/742; A61B 5/7475; B60W 40/08; B60W 10/06; B60W 10/01; B60W 2040/0827; B60W 2040/0836; B60W 2540/22; B60W 2540/24; B60W 2540/28; B60W 2550/308; B60W 2710/30; B60W 40/09; B60W 50/14
    See application file for complete search history.

(56) References Cited

U.S. PATENT DOCUMENTS

| | | | | |
|---|---|---|---|---|
| 8,408,706 B2* | 4/2013 | Yahav | .................... | A61B 3/113 351/209 |
| 9,235,987 B2* | 1/2016 | Green | ................. | G05D 1/0055 |
| 2003/0181822 A1* | 9/2003 | Victor | .................... | A61B 3/113 600/558 |
| 2005/0030184 A1* | 2/2005 | Victor | .................... | B60K 28/06 340/576 |
| 2006/0022808 A1* | 2/2006 | Ito | ......................... | G08G 1/167 340/425.5 |
| 2006/0132319 A1* | 6/2006 | Isaji | ..................... | A61B 3/113 340/576 |
| 2006/0270945 A1* | 11/2006 | Ghajar | .................... | A61B 3/113 600/558 |
| 2007/0066916 A1* | 3/2007 | Lemos | .................... | A61B 3/113 600/558 |
| 2007/0132950 A1* | 6/2007 | Victor | .................... | A61B 3/036 351/200 |
| 2008/0206727 A1* | 8/2008 | Ghajar | .................... | A61B 3/113 434/258 |
| 2011/0279676 A1* | 11/2011 | Terada | ................. | A61B 5/0006 348/148 |
| 2011/0284304 A1* | 11/2011 | Van Schoiack | ........ | B62D 1/046 180/272 |
| 2012/0262901 A1* | 10/2012 | Ichihara | ................. | B60K 35/00 362/23.18 |
| 2013/0044000 A1* | 2/2013 | Nakai | ...................... | A61B 5/18 340/575 |
| 2013/0328673 A1* | 12/2013 | Ishikawa | .................. | B60Q 1/00 340/439 |
| 2015/0130703 A1* | 5/2015 | Ghajar | .................... | G06F 3/013 345/156 |
| 2015/0228228 A1* | 8/2015 | Han | ....................... | G09G 3/005 345/690 |
| 2016/0009175 A1* | 1/2016 | McNew | ............. | H04N 13/0484 340/438 |
| 2016/0046295 A1* | 2/2016 | Wacker | ................ | A61B 3/0025 701/45 |
| 2016/0205238 A1* | 7/2016 | Abramson | ......... | G01C 21/3484 455/456.4 |

* cited by examiner

METHOD AND DEVICE FOR DETERMINING A REACTION TIME OF A VEHICLE DRIVER

FIELD OF THE INVENTION

The present invention relates to a method and to a device for determining a reaction time of a vehicle driver.

BACKGROUND

In order to determine a condition of a driver, for example under the influence of fatigue or alcohol, the reaction time and also the size of the range of vision can be included as important bases for measurement. Reaction time becomes slower when the driver is tired or under the influence of alcohol. In addition, the size of the visual field in which movements are still perceived becomes smaller. This is referred to for example as tunnel vision.

WO 93/16637 discloses a device for acquiring a reflex of a person in which a visual signal is randomly displayed at one of a plurality of predetermined recognizable locations. If the person perceives the signal, the person presses a button. The time between the displaying and the pressing of the button is the reaction time.

WO 01/52722 A1 discloses a method for recognizing the direction of view of a user, in which a light beam is directed into the eye of the user and its reflection is acquired.

SUMMARY

Up to now, no systems or methods are known that are capable of automatically acquiring the condition of a driver of a vehicle, for example automatically determining the factors noted above.

According to an example embodiment of the present invention, a method for determining a reaction time of a driver of a vehicle includes: displaying at least one visual stimulus; observing the direction of view of the driver of the vehicle using a view recognition device; determining the reaction time starting from the displaying of the visual stimulus, the reaction time corresponding to a specified time span if the direction of view of the vehicle driver is not recognized within the specified time span as going in the direction of the visual stimulus, or the reaction time corresponding to a time span in which the direction of view of the vehicle driver is recognized within the specified time span as going in the direction of the visual stimulus.

In an example embodiment, whether the visual stimulus is perceived by the vehicle driver, and, if so, when the visual stimulus is perceived by the vehicle driver is measured, and based on the measurement, the temporal difference from the beginning of the displaying of the visual stimulus up to its recognition by the driver and the driver's reaction time are determined. The method includes detecting when the direction of view of the vehicle driver runs in the direction of the location, known to the system, of display of the visual stimulus. This can for example be fulfilled if the view direction vector intersects the position of the visual stimulus, or intersects a predefined region around the position of the visual stimulus. If the driver does not succeed in recognizing the visual stimulus within a specified time span, the method, or at least the recognition of this visual stimulus, is aborted, and the reaction time is correspondingly estimated as the specified time span. This method can be carried out very easily and very reliably.

An incapacity to drive can be determined if the reaction time corresponds to the pre-specified time span, and a safety function of the vehicle can be activated. If the driver does not succeed in focusing on or observing one or more visual stimuli within the specified time span, then, for safety reasons, an incapacity to drive is determined A safety function of the vehicle can then be activated, such as locking the ignition, or outputting an acoustic warning to the driver. In this way, traffic safety can be increased.

If the driver focuses on the visual stimulus, this can be observed. A focusing on the visual stimulus can be a more detailed criterion than the acquisition of the direction of view toward the visual stimulus, thus further increasing reliability. The focusing can for example take place via observation of the pupils.

The displaying, observation, and determination can be carried out during a calibration of the view recognition device. Advantageously, in this way the calibration and the determination of the reaction time can be carried out at the same time. For the calibration, a calibration sequence can be used that is a sequence of visual stimuli, for example small circles, that appear via the display unit randomly but at positions known to the system. A camera, or a system, acquires the ocular area of the driver, and individual-specific characteristics, such as the corneal reflection, are evaluated, so that the direction of view can be determined therefrom. In this way, only one system is required in order to achieve the various goals, thus saving costs and outlay. The additional outlay for using an already-present view control system or view recognition system to measure the reaction time, or the size of the visual region still consciously perceived, is minimal. In this way, the determination or measurement of the reaction time and/or of the driver's field of vision takes place in a manner concealed from the driver. This prevents undesirable manipulation and falsification of the measurement results, for example through brief periods of particular concentration, or with the assistance of other vehicle occupants.

The view recognition device can be part of a view control device. Increasingly, view control devices are being used in vehicles, so that these systems can also advantageously be used in connection with the acquiring of the driver's condition according to example embodiments of the present invention. Under some circumstances, view control systems can produce more detailed and more precise results than can pure view recognition devices.

In an example embodiment, the duration of the specified time span is a function of the position of the displayed visual stimulus. For example, an acquisition of a visual stimulus in the central field of view can take place faster than in a peripheral area. A corresponding adaptation of the specified time span permits a more precise method.

A field of view of the vehicle driver can be determined via a distribution of the visual stimuli. From the size of the visual field in which the driver still consciously perceives actions, inferences can be made concerning the condition of the driver. If the driver is excessively fatigued or inebriated, or if so-called tunnel vision has already established itself, visual stimuli at the edge of the visual field will in part no longer be perceived at all, or the reaction time for these areas will be abnormally large. In addition to the reaction time, the field of view can be regarded as a second criterion for determining the condition of the driver. This permits an increased reliability of the method.

According to an example embodiment of the present invention, a device for determining a reaction time of a driver of a vehicle includes: a display device for displaying at least one visual stimulus; a camera for observing the direction of view of the vehicle driver; and a computing device configured to control the display device and to determine the reaction time beginning with the display of the visual stimulus, the reaction time corresponding to a specified time span if the direction of view of the vehicle driver is not recognized within the specified time span as running in the direction of the visual stimulus, or the reaction time corresponding to a time span in which the direction of view of the vehicle driver is recognized within the specified time span as running in the direction of the visual stimulus. This can be fulfilled for example if the view direction vector intersects with the position of the visual stimulus, or with a predefined region around the position of the visual stimulus. The same advantages and modifications described above hold here as well.

The display device can be situated in the region of a windshield of the vehicle. There, the visual stimuli can be detected directly by the driver, and can correspond to the actual field of view required for driving.

In an example embodiment, the display device includes at least one LED and/or a laser for displaying the visual stimulus. The LED or laser can be a component of an existing system such as a head-up display (HUD), a display such as for example a display of the central driver information system, or provided for a visualization of the stimuli in the instrument cluster. These could for example also be controlled directly by the computing device for the visualization.

Example embodiments of the present invention are explained in more detail on the basis of the drawings and the following description.

DETAILED DESCRIPTION

Figure 1:
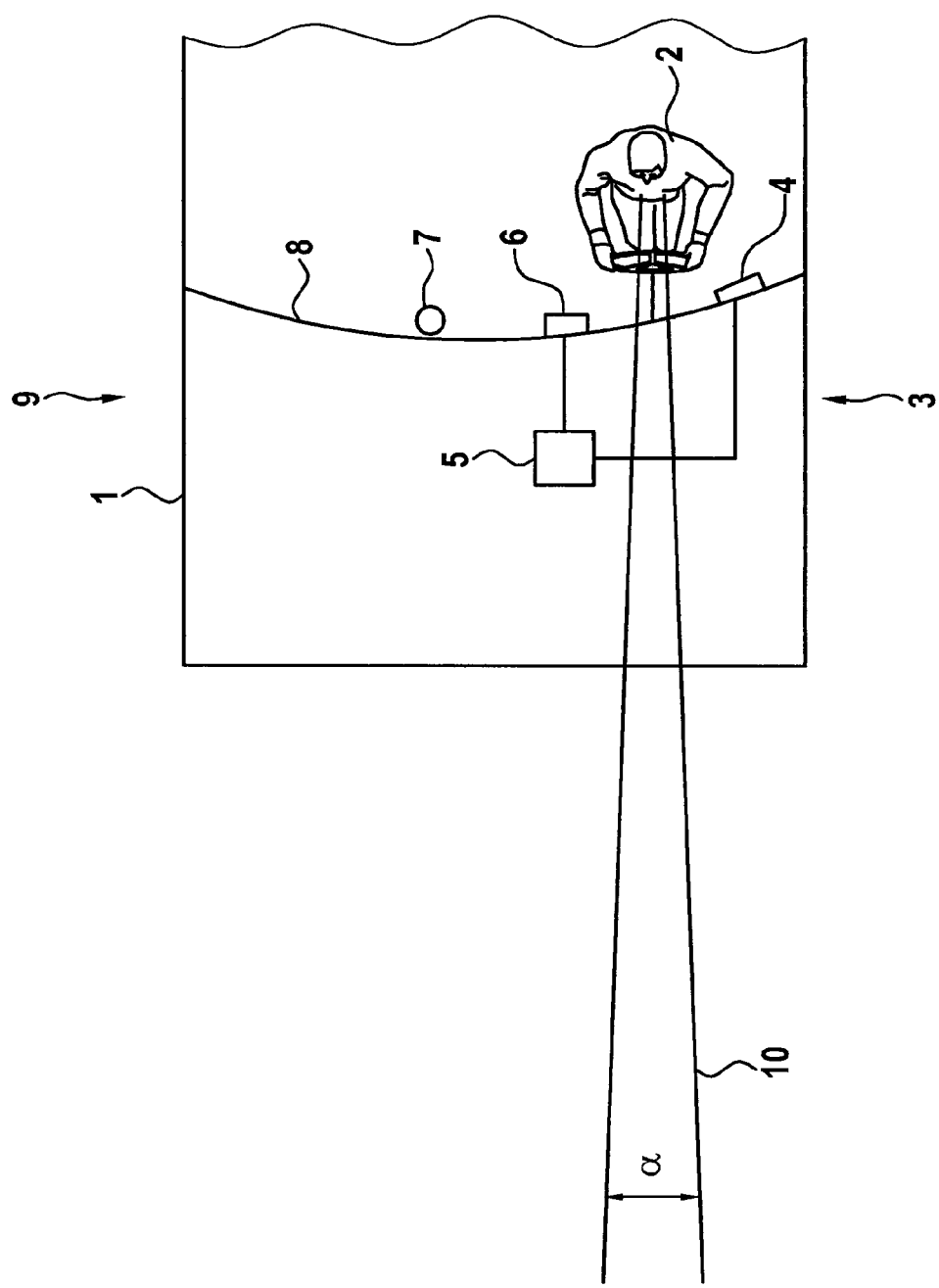
FIG. 1 shows a schematic representation of a motor vehicle including a device for determining a reaction time of a vehicle driver.

FIG. 1 shows, in a schematic representation, a front region of a vehicle 1 that is driven by, or is to be driven by, a vehicle driver 2. Here, the term "vehicle" includes land vehicles such as passenger vehicles, trucks, buses, motorcycles, etc.; water vehicles, such as ships or fairies; aircraft, such as airplanes; and railway vehicles, such as locomotives or streetcars.

A view recognition device 3, which can also be a component of a view control device, includes, in an example embodiment, at least one camera 4 for observing vehicle driver 2, in particular the face, the eyes, or the direction of view of vehicle driver 2. The camera 4 is connected to a computing device 5 that evaluates the images or signals from camera 4. In order to calibrate view recognition device 3, a display device 6 is provided with at least one visual stimulus 7, for example to display on a windshield 8 of vehicle 1. The visual stimulus 7 is for example, as shown here, a circle shown on the windshield 8.

View recognition device 3 is part of a device 9 for determining a reaction time of vehicle driver 2. The described elements of view recognition device 3, namely camera 4, computing device 5, and display device 6, can also be part of device 9 for determining the reaction time. For the recognition of the reaction time, computing device 5 is configured to determine or to measure the time between the displaying of visual stimulus 7 and the recognition of the acquisition of visual stimulus 7 by vehicle driver 2. This time duration corresponds to the reaction time of driver 2.

In addition, computing device 5 is set up to detect a region of view 10 or field of view, or an angular region of view 10, of the vehicle driver 2. For this purpose, various optical or visual stimuli 7 are distributed along windshield 8 in order in this way to determine the boundaries of region of view 10 of driver 2. In FIG. 1, a so-called tunnel vision situation is shown, which is distinguished by a small angle α and which permits the inference that driver 2 is under the influence of alcohol or is tired.

Figure 2:
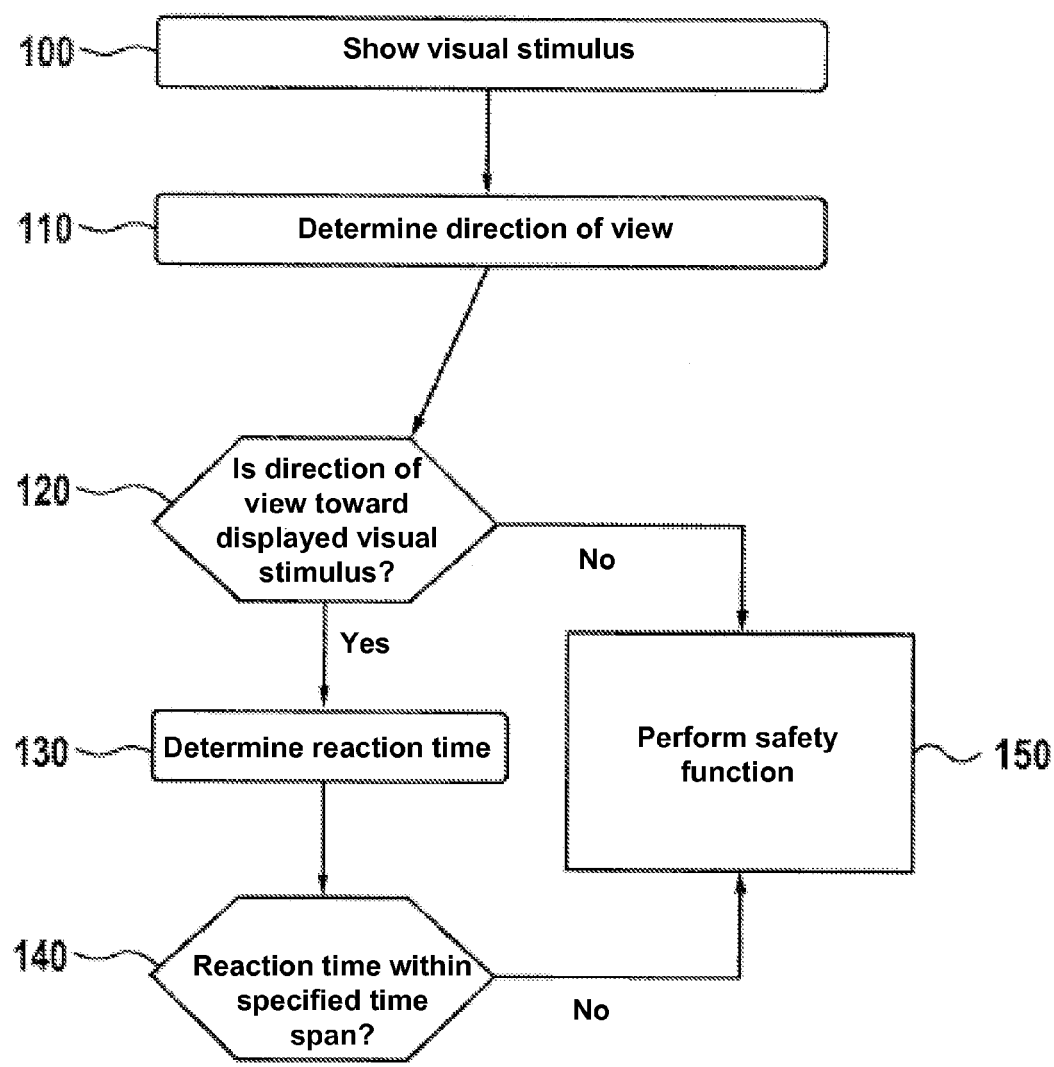
FIG. 2 is a flowchart that illustrates a method for determining a reaction time of a vehicle driver.

On the basis of FIG. 2, the method for determining the reaction time of driver 2 is now explained in more detail. In a first step 100, a visual stimulus 7, or a plurality of visual stimuli 7, are shown on windshield 8 in the field of view of driver 2. The location of display of visual stimulus 7, i.e., the position on windshield 8 in terms of height and lateral orientation, i.e., transverse to a direction of travel of vehicle 1, is controlled by computing device 5. For vehicle driver 2, the display of visual stimuli 7 takes place in a random manner. Computing device 5 can however cause visual stimuli 7 to be displayed according to a program, in order for example to determine region of view 10 of vehicle driver 2.

In a second step 110, the direction of view of the vehicle driver 2 is observed or determined Using one or more cameras, for example, the eye movements of driver 2 are tracked, and in this way the direction of view of driver 2 is determined.

In a further step 120, it is determined whether the direction of view of driver 2 runs in the direction of displayed optical stimulus 7, or whether the view direction vector intersects with the position of the visual stimulus, or with a predefined region around the position of the visual stimulus. Alternatively or in addition, it can be determined whether driver 2 is focusing on visual stimulus 7.

If this is the case, then in a further step 130 the temporal difference is determined or measured between the beginning of the display and acquisition by vehicle driver 2. This temporal difference corresponds to the reaction time of driver 2. The reaction time begins when display device 6 displays, in response to an activation of computing device 5, a visual stimulus 7, for example on windshield 8. The time span ends when camera 4, or computing device 5, determines that driver 2 has acquired or recognized visual stimuli 7.

In a further step 140, it is determined whether the acquisition by the driver, or, expressed differently, the reaction time of driver 2, is within a specified time span. This time span or time window interrupts the acquisition of visual stimulus 7 by driver 2, or the determination of the reaction time. This acts to exclude excessively long reaction times, given which the driver of the vehicle is not capable of driving, or is capable of driving only to a limited extent.

This predetermined time span can be in the range of seconds, or fractions of seconds. If the predetermined time span is used to determine an incapacity to drive on the part of vehicle driver 2, then its length or duration is measured using criteria of capacity or incapacity to drive. The length of the predetermined time span can be varied by computing device 5, and in this way for example each position of the visual stimulus can have its own predetermined time span. Alternatively, in an example embodiment, particular zones, for example a central region of windshield 8, as well as lateral regions of windshield 8, are assigned different predetermined time spans. Finally, in an example embodiment, the time window is adapted to the calibration process, because particular time sequences have to be taken into account for a calibration.

If in step 140 a normal reaction time is recognized, i.e., the reaction time is below or within the specified time span, then driver 2 can start vehicle 1 and can begin to travel. Preferably, in an example embodiment, the method described here takes place in the context of a calibration of view recognition device 3 before starting vehicle 1.

If the specified time span is exceeded, then in a further step 150 a safety function of the motor vehicle 1 is called; for example, the ignition is locked and/or a warning is outputted to driver 2. This step 150 is also carried out if in step 120 visual stimulus 7 is not acquired, or is incorrectly acquired, by driver 2. The two steps 120 and 140 can be combined with each other, so that already at step 120 branching takes place to step 150 if the specified time span is exceeded.

What is claimed is:

1. A method for determining a reaction time of a driver of a vehicle, the method comprising:
   displaying, by a display device, at least one visual stimulus;
   processing, by processing circuitry, a sensor output to determine a direction of view of the driver by using one or more cameras to track eye movements of the driver;
   determining, by the processing circuitry, a reaction time beginning at an initial display, in the displaying step, of the at least one visual stimulus, wherein the determining is performed according to conditions such that:
      the reaction time is determined to equal a predetermined time span if the direction of view of the driver is not recognized within the predetermined time span as being in the direction of the visual stimulus, and
      the reaction time is determined to be an actual recorded time span in which the direction of view of the driver is recognized as being in the direction of the visual stimulus if the recognition occurs within the predetermined time span, wherein the actual recorded time is a temporal difference between a first time corresponding to the initial display of the visual stimulus and a second time corresponding to when the direction of view of the driver is recognized as being in the direction of the visual stimulus; and determining a field of vision of the driver, wherein:
      a duration of the predetermined time span varies as a function of a position of the visual stimulus in the field of vision, and
      the duration is larger when the visual stimulus is in a peripheral area of the field of vision than when the visual stimulus is in a central area of the field of vision.

2. The method of claim 1, further comprising:
   activating a safety function of the vehicle to address an incapacity of the driver to drive if the reaction time is determined in the determining step to equal the predetermined time span.

3. The method of claim 1, further comprising determining whether the driver is focusing on the visual stimulus.

4. The method of claim 1, wherein the displaying, processing, and determining are carried out during a calibration of a view recognition device used for the determination of the direction of view.

5. The method of claim 1, the determination of the direction of view is performed using a view recognition device that is part of a view control device.

6. The method of claim 1, wherein the at least one visual stimulus includes a plurality of visual stimuli displayed at different locations, and the predetermined time span varies depending on the respective positions at which the visual stimuli are displayed.

7. The method of claim 1, wherein the at least one visual stimulus includes a plurality of visual stimuli displayed at different locations, and the method further comprises determining a field of vision of the driver based on a distribution of the locations of the visual stimuli.

8. The method of claim 1, wherein:
   the field of vision measures a visual field in which the driver consciously perceives actions, and
   the driver is deemed fatigued if the reaction time equals at least the predetermined time span and if an angular extent of the field of vision is smaller than a predetermined angle.

9. A device for determining a reaction time of a driver of a vehicle, the device comprising:
   a display device;
   a camera; and
   processing circuitry in communication with the camera and the display device, wherein the processing circuitry is configured to:
      control the display device to display at least one visual stimulus;
      process output of the camera to determine a direction of view of the driver; and
      determine a reaction time beginning at an initial display, in the displaying step, of the at least one visual stimulus, wherein the determining is performed according to conditions such that:
         the reaction time is determined to equal a predetermined time span if the direction of view of the driver is not recognized within the predetermined time span as being in the direction of the visual stimulus; and
         the reaction time is determined to be an actual recorded time span in which the direction of view of the driver is recognized as being in the direction of the visual stimulus if the recognition occurs within the predetermined time span, wherein the actual recorded time is a temporal difference between a first time corresponding to the initial display of the visual stimulus and a second time corresponding to when the direction of view of the driver is recognized as being in the direction of the visual stimulus, wherein:
         the processing circuitry determines a field of vision of the driver,
         a duration of the predetermined time span varies as a function of a position of the visual stimulus in the field of vision, and
         the duration is larger when the visual stimulus is in a peripheral area of the field of vision than when the visual stimulus is in a central area of the field of vision.

10. The device of claim 9, wherein the display device is situated for displaying the at least one visual stimulus on a windshield of the vehicle.

11. The device of claim 9, wherein:
    the field of vision measures a visual field in which the driver consciously perceives actions, and
    the driver is deemed fatigued if the reaction time equals at least the predetermined time span and if an angular extent of the field of vision is smaller than a predetermined angle.

12. The device of claim 9, wherein the display device includes at least one of a laser and at least one LED for displaying the at least one visual stimulus.

13. A safety method based on a reaction time of a driver of a vehicle, the method comprising:
displaying, by a display device, at least one visual stimulus;
processing, by processing circuitry, a sensor output to determine a direction of view of the driver;
determining, by the processing circuitry and based on the determined direction of view, whether a driver reaction time, beginning at an initial display, in the displaying step, of the at least one visual stimulus, is less than a predetermined time span;
performing a safety action when the determination in the determining step is that the driver reaction time is not less than the predetermined time span, wherein the driver reaction time is a temporal difference between a first time corresponding to an initial display of the visual stimulus and a second time corresponding to when the direction of view of the driver is determined as being in a direction of the visual stimulus; and
determining a field of vision of the driver, wherein:
a duration of the predetermined time span varies as a function of a position of the visual stimulus in the field of vision, and
the duration is larger when the visual stimulus is in a peripheral area of the field of vision than when the visual stimulus is in a central area of the field of vision.

14. The safety method of claim 13, wherein:
the field of vision measures a visual field in which the driver consciously perceives actions, and
the driver is deemed fatigued if the reaction time equals at least the predetermined time span and if an angular extent of the field of vision is smaller than a predetermined angle.

* * * * *